(12) United States Patent
Miller et al.

(10) Patent No.: US 7,995,205 B2
(45) Date of Patent: Aug. 9, 2011

(54) VISUALIZING BIREFRINGENT STRUCTURES IN SAMPLES

(75) Inventors: Peter Miller, Cambridge, MA (US); David Fletcher-Holmes, Boston, MA (US); Cathy M. Boutin, New Ipswich, NH (US); Clifford Hoyt, Wellesley, MA (US)

(73) Assignee: Cambridge Research & Instrumentation, Inc., Woburn, MA (US)

( * ) Notice: Subject to any disclaimer, the term of this patent is extended or adjusted under 35 U.S.C. 154(b) by 404 days.

(21) Appl. No.: 12/273,299

(22) Filed: Nov. 18, 2008

(65) Prior Publication Data

US 2009/0135422 A1    May 28, 2009

Related U.S. Application Data

(60) Provisional application No. 61/003,692, filed on Nov. 19, 2007.

(51) Int. Cl.
*G01J 4/00* (2006.01)
(52) U.S. Cl. .................................................. 356/364
(58) Field of Classification Search ............ 356/364; 250/559.09
See application file for complete search history.

(56) References Cited

U.S. PATENT DOCUMENTS

| | | | |
|---|---|---|---|
| 5,521,705 A | 5/1996 | Oldenbourg et al. | |
| 7,202,950 B2 | 4/2007 | Shribak et al. | |
| 7,239,388 B2 | 7/2007 | Shribak et al. | |
| 7,372,567 B2 * | 5/2008 | Shribak et al. | 356/364 |
| 2005/0007590 A1 * | 1/2005 | Shribak et al. | 356/364 |
| 2007/0171419 A1 * | 7/2007 | Shribak et al. | 356/364 |

* cited by examiner

*Primary Examiner* — Roy Punnoose
(74) *Attorney, Agent, or Firm* — Cohen Pontani Lieberman & Pavane LLP (57) ABSTRACT

Apparatus and methods are disclosed for viewing low-birefringence structures within samples directly, with the eye, in real-time. The sample is placed between an entrance polarizer and analyzer polarizer, the transmission state of one of which is changed dynamically to create a modulated view of the scene; against this background, birefringent structures are visible because of their different appearance when modulated. Modulation rates of 4 or more states per second; use of 4 or more states, or even a continuum of states, which lie substantially on a latitude line on the Poincare sphere; and orientation of the polarization components to produce a uniform background; produce a clear view that does not produce operator fatigue. Broad-band wavelength operation spanning 50 nm or more, or the whole visible range, is achieved, and it is compatible with integration into other microscopy modes such as Hoffman relief contrast.

14 Claims, 4 Drawing Sheets

VISUALIZING BIREFRINGENT STRUCTURES IN SAMPLES

RELATED APPLICATIONS

This application claims priority from U.S. Provisional Patent Application Ser. No. 61/003,692, which was filed on Nov. 19, 2007. The entire contents of application 61/003,692 are incorporated herein by reference.

BACKGROUND OF THE INVENTION

1. Field of the Invention

The present invention is related to the use of polarized light to visualize structures that possess molecular order or that are under strain.

2. Description of the Related Art

Materials having a different optical index of refraction for different states of polarization are said to express birefringence, and the amount of birefringence in a sample is termed its optical retardance. The index of refraction is highest for rays of light having an E field along a first direction, which is termed the fast axis for that sample. It is conventional to describe that direction as the azimuth angle, relative to some coordinate system of interest.

Polarized light has been used to obtain contrast in light microscopy. One benefit of this arrangement is that it enables one to obtain contrast with unstained samples. Common arrangements include use of a pair of crossed polarizers in the beam path, with one polarizer placed prior to the sample and one after it. The sensitivity of these methods is limited, and it is difficult to detect retardance is below 5 nm.

The Poincare sphere is an established way of representing state of polarization, where each point on the sphere indicates a unique polarization state of light. The longitude $2\theta$ and latitude $2\epsilon$ of a point on the sphere correspond to a polarization ellipse with azimuth $\theta$ and ellipticity angle $\epsilon$. The ellipticity angle is an auxiliary angle that specifies the shape of the vibration ellipse, via the equation $\tan \epsilon = b/a$, where a and b are the major and minor semi-axes of the ellipse. Thus, lines of constant longitude and latitude on the sphere represent contours of equal azimuth and equal ellipticity, respectively. The Northern hemisphere represents light with right-hand elliptical polarization, and the Southern hemisphere represents left-hand elliptically polarized light.

In U.S. Pat. No. 5,521,705, Oldenbourg and Mai teach apparatus for calculating the optical retardance and azimuth angle at many locations in an unstained birefringent sample, and produce images of the sample based on this information. The apparatus illuminates a sample with quasi-monochromatic light that is approximately circularly polarized, and measures the intensity of light after it passes through an approximately circular analyzer polarizer. From four measurements of intensity, using slightly different polarization states at the illuminator polarizer or the analyzer polarizer, the birefringence properties of the sample are calculated and an image is displayed. One of the four measurements is taken with the two polarizers configured to produce substantially the best extinction possible; this configuration is termed the extinction state.

In U.S. Pat. No. 7,202,950 and U.S. Pat. No. 7,239,388, Oldenbourg and Shribak teach techniques for obtaining optical retardance and azimuth angle based on 2, or 3, or 5 measurements of a birefringent sample. They also teach the use of four measurements, where none of the states corresponds to the extinction state.

Cambridge Research and Instrumentation, Inc (Woburn, Mass.) manufactured the SpindleView and LcPolScope systems using the Oldenbourg and Mai technique, using a video camera and a personal computer to generate images of samples viewed in a microscope. Two liquid crystal cells and a linear polarizer are used to construct either the entrance polarizer or the analyzer polarizer. One of the liquid crystal cells provides approximately ½ wave of retardance, and the other provides approximately ¼ wave of retardance. The azimuth angles of the two cells are offset from one another by 45 degrees. An interference filter transmits a 30 nm band centered at 546 nm through the apparatus.

The software performs a calibration cycle wherein the video camera output is digitized and measured while the liquid crystal cells are driven to a variety of states. Based on the readings obtained under various trial conditions explored in this way, the software determines what are suitable settings for the liquid crystal cells. This calibration takes 30-60 seconds and must be performed before any of the normal operating functions are available. Once calibration is performed, these systems require approximately 2 seconds to acquire the video images, calculate an image of a sample, and produce an image on a computer display.

The SpindleView software has a button which engages or disengages a blinking mode. Calibration must have been performed beforehand. In blinking mode, the computer drives the liquid-crystal based polarizer between two states in alternation, which produces a blinking view at the microscope eyepieces. The blink rate is adjustable from about 1 state/second to a maximum of approximately 2.6 states/second via a software slider control. An observer looking through the microscope eyepieces sees the entire field of view change brightness, due to the changing configuration of polarizers. The view is not uniform: one sees markedly darker and lighter regions, and as the polarizer switches state, regions that were brighter may become darker, or their brightness may be unchanged. Also, while the image has an overall green appearance, there can be changes in hue, ranging from blue-green to yellow-green as different components of the imperfectly-pure green light vary in proportion. The details of what patterns are seen, and how they change during blinking, are unpredictable.

Nonetheless, within this blinking field, a skilled observer can learn to detect birefringent structures by their different blink signature: as the polarizer state is alternated, birefringent structures exhibit a greater or lesser degree of brightness (or color) change than do their surroundings. This is an unsatisfactory arrangement for several reasons: it is visually tiring due to the stroboscopic blink action; some people never attain competence at resolving structures against the background, or attain only limited competence so can only see the most highly birefringent structures; and the variable and uncontrolled nature of the spatial patterns make it hard to predict whether good results will be obtained in any given setup.

The Oosight system from Cambridge Research & Instrumentation (Woburn, Mass.) uses one or more of the techniques of Oldenbourg and Mai, or of Oldenbourg and Shribak, to produce computer-calculated images of birefringence in samples. The liquid crystal, polarizer optics, and interference filter are substantially the same as in the SpindleView system. This system has a live mode in which it takes approximately 3 images per second and displays calculated images to the computer display at this rate. It must perform a calibration step, similar to that in the SpindleView, prior to normal operation, during which the digitized images from the camera are measured by the computer software while the liquid crystal cell settings are adjusted.

The Abrio system from Cambridge Research & Instrumentation (Woburn Mass.) uses one or more of the techniques of Oldenbourg and Mai, or of Oldenbourg and Shribak, to produce computer-calculated images of birefringence in samples. The optics in this system differ from the Oosight, SpindleView and LcPolScope in that its entrance or analyzer polarizer incorporates three liquid crystal cells rather than two, together with a linear polarizer. Two of the cells are configured adjacent to one another with their azimuth angles offset by 90 degrees so they largely cancel one another, and produce a net retardance equal to the difference of their individual retardance values. Consequently, the arrangement has a retardance close to zero; the third liquid crystal cell has a retardance of ¼ wave and its azimuth angle is 45 degrees from either of the paired elements. Again, a narrow-band interference filter is used to produce monochromatic light from a source; either a 10 nm bandwidth or 30 nm bandwidth is used. It must perform a similar calibration step to that of the Oosight system.

These systems have been used in the fields of biology [Katoh 1999 Proc. Natl. Acad. Sci. USA. 96:7928-7931, LaFountain 2001 Mol Biol Cell 12:4054-4065], materials science [Hoyt 1999 American Laboratory. 31(14):34-42] and medicine [Keefe 2003 Reprod Biomed Online 7(1):24-9, Shen 2005 Human Reproduction].

Keefe reported that the Oldenbourg and Mai technique can be used to detect, locate, and evaluate the condition of organelles within oocytes. Shen has used it for quantitative assessment of these structures. In particular, a structure called the spindle can conveniently be detected in this way, though it is ordinarily invisible. The physical origin of the optical retardance in such structures arises from the fact that their molecular arrangement is ordered, which gives rise to birefringence.

In the field of somatic-cell nuclear transfer, where oocytes are enucleated to serve as hosts for DNA from an organism that is to be cloned, practitioners report using the Oldenbourg and Mai apparatus to assist with visualization of the spindle [Wang 2002 Cloning Stem Cells 4(3):269-76]. Mitalipov reported successful cloning of a monkey to produce stem cells, in a process where the Oosight apparatus was used as an aid during enucleation, to locate the spindle.

MTG Medical Technology (Altdort, Germany) sells the ICSI-Guard system for use in embryology and in vitro fertilization procedures. It includes a camera and image digitizer which takes images of a sample using polarized light, and produces a computer-generated image of structures in the sample on a display.

Schimming and Rink teaches apparatus for polarized light imaging in WO2006/081791.

Structures in unstained samples can be observed using other methods, such as differential interference contrast, phase contrast, interferometry, Nomarski contrast, and Hoffman contrast. However, each of these has strengths and weaknesses, and in general no one technique is effective in all cases. All are of limited value for observing spindle structures in oocytes.

The apparatus of the prior art provides for measurement of birefringent structures at rates ranging from several seconds per image, to approximately 3 images per second. It also provides for a visual detection of birefringent structures based on interpretation of a blinking eyepiece view of a sample by a skilled operator while polarizers are alternately driven between different states, at rates up to approximately 3 states/second. This art involves complicated and costly systems with a digitized camera and a personal computer; first to perform the initial calibration and setup; and then, to perform the measurement of intensity, calculate the sample retardance, and generate an image on a computer display. Where a quasi-real-time view is available, it is provided at a computer display so the microscopist must shift attention from the microscope to the display; or yet more complex systems must be devised which project or merge the computer-generated image into the eyepiece view. Where an eyepiece view is provided, it is of limited value for reasons such as those noted above, and the green-light view it affords is undesirable to some users.

Indeed, in the prior art for measuring low birefringence structures in samples, the use of quasi-monochromatic light is integral to the measurement. Yet this interferes with other uses of the microscope for several reasons. First, switching to any white-light mode requires at least the removal of the filter element, or the reconfiguration of the illuminator, so as to obtain a white-light view. Where this is done via a filter, the microscopist suddenly is presented with a much brighter view than before, since the entire illumination flux is now seen, rather than just a small portion of the green component. This can lead to uncomfortable, even painful, glare and a period of accommodation.

Also, the prior art methods have inherently low transmission, since they use polarizers operated near their extinction point. Consequently, microscopists choose a relatively bright setting for the microscope lamp, to provide an adequately bright view. Switching to a different microscopy mode such as bright field, Nomarski, or Hoffman (relief) contrast may require removing one or more of the polarizers from the beam. Without the polarizer extinction, the signal in the eyepieces becomes much brighter. When this is combined with the brightness increase from switching to white light from quasi-monochromatic green light, the signal is vastly different in the configuration where birefringent structures are visible, from that in other microscopy modes. Often the microscopist needs to adjust the lamp or introduce attenuators to obtain a satisfactory view. This sort of adjustment is in addition to the adjustment whereby the polarizer must be removed from the beam or reconfigured in some way. So changing between the birefringence imaging modes of the prior art, and other microscopy modes often involved several user adjustments and significant brightness adjustment or changes.

There are many areas of technical work where a microscopist uses multiple imaging modes. This is because certain tasks are more readily performed with a particular view of the specimen. For example, someone performing in vitro fertilization may prefer to use a prior art birefringence imaging method such as the Oosight to view the spindle, but prefer to use a different contrast technique such as Hoffman contrast for egg manipulation.

In the prior art, the two modes may not be employed simultaneously, for several reasons. First, there is a tremendous light loss if both systems are engaged. The prior art system of Oldenbourg uses circularly polarized quasi-monochromatic light, such as a 30 nm band in the green centered on 546 nm. Overall, less than 10% of the total visible light reaches the sample—all other wavelengths are discarded, as is light in the complementary polarization state. Then, light must pass through the analyzer polarizer, which is set to an operating point near extinction, so it transmits only 2%-5% of the light reaching it. Overall, the apparatus transmits 0.2-0.5% as much light as a simple transmitted light setup, and light levels are often marginal for this apparatus, especially when operated with high magnification objectives such as 20× or higher.

The Hoffman arrangement requires placing a patterned mask at the back focal-plane of the objective, and another at a conjugate plane on the illumination optics side; these further attenuate the light approximately 10-fold. Part of the loss is because numerical aperture is reduced, and part is because neutral-density elements or linear polarizers are cover some of the pattern area.

The combination of all these losses leads to an unusably dark image.

Second, some modalities use polarized light optics in ways that conflict with the polarization measurements of the prior art birefringence imaging systems. For example, some Hoffman implementations incorporate an adjustable linear polarizer on the illumination side, which works in concert with a linear polarizer covering one or more slots of the slotted mask. These form a variable attenuator, where the user rotates the adjustable linear polarizer to achieve an optimum sample view, based on the degree of attenuation and the image produced.

The prior art apparatus utilizes a circular polarizer on the illumination side, and teaches circular polarizers consisting of a linear polarizer followed by a quarter wave plate. The variable linear polarizer interacts with the linear polarizer within the circular polarizer in undesirable ways. For example, it is possible to achieve a setting where no light at all passes through the system because these two polarizers are crossed. Yet that setting of the variable linear polarizer may correspond to the optimum sample view setting for Hoffman imaging.

SUMMARY OF THE INVENTION

It is a goal of the present invention to overcome the limitations of the prior art, including cost, complexity, and where the computed display is relied upon, the slow update rate and need to shift one's view from the eyepieces to the display; and where eyepiece viewing is relied upon, the problem of poor acuity when resolving low-birefringence structures from a complex, blinking scene; or visual strain; or low light level; or unpredictable results; or the limitations of quasi-monochromatic viewing; or limited compatibility with other modes of microscopic imaging; or various combinations of these.

In one aspect, the present invention provides an eyepiece viewing system where microscopists can readily identify and locate low-retardance birefringent structures without excessive visual strain. In one embodiment, a view is provided where the microscopist sees 5 or more polarization states per second.

In another embodiment, the polarization states describe a continuous arc on the Poincare sphere and a more comfortable view is produced.

In another, the microscopists sees 6 or more states which are approximately evenly spaced about a latitude line on the Poincare sphere, within 20 degrees of either pole. In some embodiments, 16 states or more are used and a nearly continuous visual appearance is produced.

In some embodiments, as many as 32 or even 80 states per second are displayed, to provide a rapid, but visually continuous, modulation of the signal in the eyepieces.

In some embodiments, the system traverses polarization states at a variable rate which the user selects by a control, to achieve a desired visual display. In some embodiment, the latitude of the states on the Poincare sphere is selectable, producing an adjustable depth of polarization modulation.

In some embodiments, the states are traversed in the same direction on the Poincare sphere, such as always progressing east, or always west.

In another aspect, the present invention provides for a eyepiece viewing system for birefringent structures where the light presented to the microscopist spans range that is markedly broader than the 30 nm of the prior art, and instead spans a range of 50 nm or more; or 100 nm or more; or even a range which substantially spans the visible range and gives a natural, white-light appearance. This provides for higher throughput, or more comfortable view, or compatibility with other microscopy modes, or more similar light levels when switching between microscopy modes, or some combination of these.

In one embodiment, this is accomplished by constructing and orienting the entrance polarizer and analyzer polarizer in such a way that the chromatic effects of each element are canceled by the other. With chromatic effects absent or greatly reduced, broadband or white light can be employed instead of quasi-monochromatic light, and in some embodiments a white light view is attained.

In one embodiment this is attained through use of a linear polarizer and quarter wave plate as the entrance polarizer, with absorption and fast axis orientations of 0 and 45 degrees, respectively, as viewed by a ray traversing forward along the optical axis of the system; and an analyzer polarizer made of a quarter wave plate and linear polarizer having fast axis orientation at substantially 135 degrees, followed by a linear polarizer; where the analyzer polarizer contains electro-optic elements which effect slight changes to its polarization response which cause the maximally transmitted polarization state to traverse points lying substantially along a latitude line on the Poincare sphere, within 20 degrees of either pole.

In a preferred embodiment, the electro-optic element comprises one or more liquid crystal cells.

In other embodiments, the construction and orientation of the entrance polarizer and analyzer polarizer are chosen to minimize or cancel chromatic effects within a quasi-monochromatic view.

In other embodiments, the entrance polarizer produces slight changes in its polarization state and the analyzer polarizer has fixed response as a substantially circular polarizer.

In other embodiments, mechanical apparatus is taught in which a retarder or elliptical polarizer is rotated so the polarization state maximally transmitted rotates along a path that is substantially along a given latitude line on the Poincare sphere, and lies within 20 degrees of one of the poles.

In yet other embodiments, the invention provides for methods of constructing and installing an eyepiece viewing system for low-birefringence structures comprising two polarizers where no calibration steps are necessary, except for a rotational alignment step where the relative rotation of the polarizers to minimize fluctuations in chromatic response, or brightness, or both, in the eyepiece view.

In other embodiments, the invention provides apparatus and methods for an eyepiece viewing system where the user adjusts the drive signals to the liquid crystal cells based on a visual assessment of when the image in the eyepieces is darkest.

In yet other embodiments, the user adjusts the drive signals to the liquid crystal cells based on a visual assessment that the light levels in the scene vary the least while the states are cycled repeatedly through a path that forms substantially a latitude line on the Poincare sphere when properly set.

In yet other embodiments, one or more of the circular polarizers in an eyepiece viewing system for birefringent structures has quarter-wave plates sandwiched adjacent on both sides of a linear polarizer, and is placed in optical series with a variable rotation linear polarizer, so the transmission of the overall assembly is not markedly affected by the variable polarizer orientation.

In one embodiment of this type, the eyepiece viewing apparatus is placed on a microscope which incorporates Hoffman optics, and the circular polarizer having the sandwich construction is placed on the illumination side. In one of these embodiments, the illumination-side mask, bearing a linear polarizer on one or more slots, is interposed between the variable linear polarizer and the circular polarizer having the sandwich construction. Rotation of the variable linear polarizer adjusts the light level through the polarizer-bearing slots of the Hoffman mask, but the light level through other slots is not affected. Accordingly this embodiment is compatible with simultaneous Hoffman imaging and eyepiece viewing of birefringent structures.

In one embodiment of this type, the system transmits light over a wide spectral range such as 50 nm or more, or even 100 nm or more, and high light levels are obtained.

Further explanation is given below with reference to the following drawings, in which like reference characters denote similar elements throughout the various Figures.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

In the drawings, like reference characters denote similar elements through the several views.

DETAILED DESCRIPTION OF THE PRESENTLY PREFERRED EMBODIMENTS

The invention concerns use of two elliptical polarizers, one of which exhibits a time-varying ellipticity, to visualize birefringent structures in samples. This produces a time-modulated visual scene, in which birefringent structures are evident because their appearance is different from the background.

Figure 1:
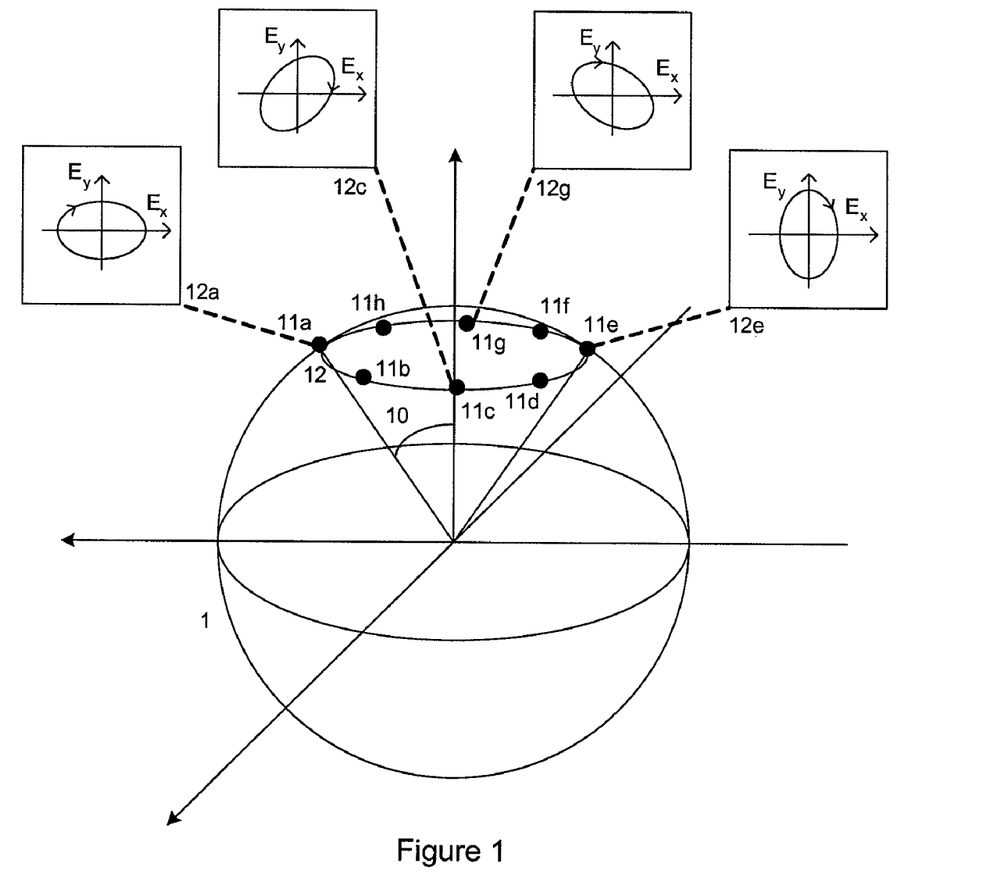
FIG. 1 depicts the Poincare sphere 1, with states 11a-11h spaced approximately equally spaced along a line of constant latitude 12 situated at an angle 10 from the North pole. The electric field ellipses corresponding to states 11a, 11c, 11e, and 11g are depicted as 12a, 12c, 12e, and 12g.

One aspect of the invention is to provide modulation between four or more states that lie substantially on the same latitude on the Poincare sphere, as illustrated in FIG. 1. In this embodiment, either the entrance polarizer or analyzer polarizer is substantially a circular polarizer corresponding to the South pole on the Poincare sphere, and the other polarizer expresses the points 11a, 11c, 11e, and 11g. The poles may be reversed, so that the circular polarizer is substantially located at the North pole of the Poincare sphere while the other polarizer executes a series of states surrounding the South pole. What is important is that one polarizer be substantially a circular polarizer located at one pole of the Poincare sphere, and the other executes a series of states surrounding the antipodal pole of the Poincare sphere.

In the preferred embodiment, the angle 10 is less than 20 degrees, and is preferably in the range 3-15 degrees. In some embodiments, the invention uses 8 states, such as 11a-11h, or even 16 states, where the additional states are interpolated between those shown, to form a relatively even spacing around the latitude ring 12.

The use of many states rather than the two states of the prior art produces a modulation which is relatively smooth, rather than choppy, and reduces visual strain.

The states are produced in longitude sequence, so that the polarizer traverses a ring around the Poincare sphere. This ring may be traversed in either direction, Eastward or Westward, without changing the degree to which birefringent structures can be seen.

As the number of states grows, the apparatus preferably cycles through the various states at a faster rate (less time per state) so the progress around the ring remains relatively rapid. In one preferred embodiment, the apparatus makes a complete trip around the sphere at a rate of 0.5 Hz-5 Hz, recognizing that individual operators may have personal preferences.

The choice of cycle rate may also depend on factors such as the task being performed and the individual sample at hand. A more rapid rate is preferred when manipulating samples; for example, in embryology tasks such as during enucleation and egg manipulation; while a slower rate may be preferred for studying or observing the sample. The operator may also wish to change the latitude ring 12 associated with the polarizer states. A ring located farther from the pole produces a greater amount of modulation, while moving closer to the pole reduces the modulation depth; this can be beneficial to accommodate samples with a higher or lower degree of birefringence. The invention may include controls such as knobs, buttons, or sliders for the operator to change cycle rate or Poincare latitude; on versions of the invention where the apparatus is controlled by software on a personal computer, these can be elements in the graphical user interface (GUI) of a program or control dialog, or they may be implemented by trackballs, mouse controls, or dedicated keys.

In one preferred embodiment, 16 equally spaced states were defined lying on latitude ring 12 with an angle 10 of 11 degrees, corresponding to a latitude of 79 degrees North on the Poincare sphere. These were cycled at rates ranging from 16 to 100 states per second, and a smooth visual appearance was produced. Mouse oocytes were observed with this apparatus, using a heated stage and a 40× objective, and unskilled observers could readily observe the structures associated with the spindle and the zona pellucida. With this apparatus, the motion appeared smooth rather than quantized into steps.

Subjectively, the use of four or more states produces a less choppy appearance than the two states of the prior art, and the eye is drawn to the birefringent structures not by a single abrupt change, but rather by the repeated, periodic pattern of lightening and darkening which they express.

Figure 2:
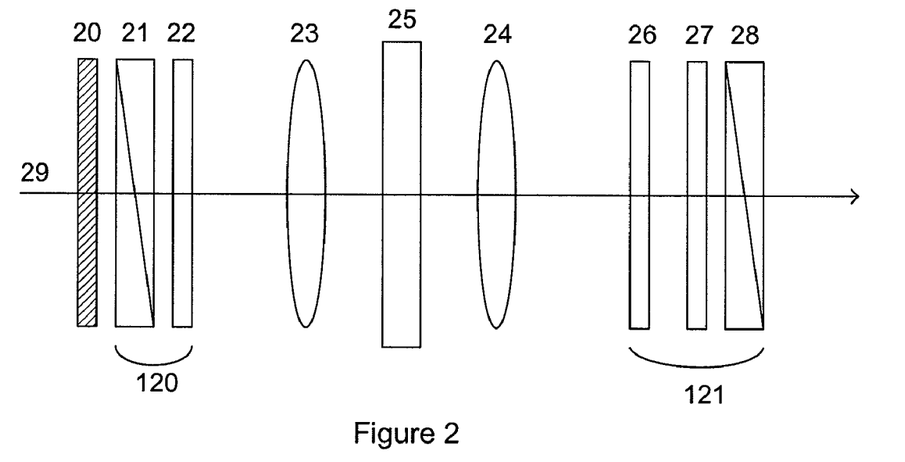
FIG. 2 is a schematic drawing implementing the invention in a first optical arrangement. Incident light traveling along optical axis 29 passes through optional optical filter 20, then through entrance polarizer 120 which in this embodiment comprises linear polarizer 21 and retarder 22; optional illumination optics 23 deliver the light to sample 25 and optional imaging optics 24 direct it to analyzer polarizer 121 which in this embodiment comprises retarder 26, retarder 27, and linear polarizer 28.

The apparatus shown in FIG. 2 can be used to realize the invention. For example, entrance polarizer 120 can be using quarter wave plate retarder for 22, with its fast axis is oriented at 45 degrees to the absorption axis of linear polarizer 21. A suitable retarder material for 22 is the quarter-wave retardance film offered by Nitto Denko (Fremont, Calif.). A suitable linear polarizer is available from Sanritz, model LLC2-5618. Together, these produce light which is nearly circularly polarized for $\lambda\sim 550$ nm, and somewhat elliptical at other wavelengths.

Bandpass filter 20 may be an interference filter with bandwidth of 30 nm, centered on 546 nm, available from Omega Optical (Brattleboro, Vt.). Illumination optics 23 may be the IX2-MLWCD condenser of an Olympus IX-71 microscope, and imaging optics 24 may be a 40× UPLSAPO objective. The sample 25 may be a mammalian oocyte, or another kind of living cell, contained in a glass-bottomed sample dish such as a Willco Wells 35 mm or 50 mm dish, available from Warner Instruments (Hamden, Conn.).

Analyzer polarizer 121 can be realized using a retarder 26 which is a liquid crystal variable retarder (LCVR) having approximately ½ wave retardance, with its fast axis oriented at angle α, a retarder 27 which is an LCVR having its fast axis at an orientation 45 degrees offset from that of element 26 and having approximately ¼ wave retardance, followed by linear polarizer 28 made of Sanritz model LLC2-5618 material. The LCVR can be pi-cell or flat-field type, as is known in the liquid crystal device art. Suitable cells and drive electronics can be obtained from Meadowlark Optics (Longmont, Colo.).

One may then drive the LCVR elements as follows:

TABLE 1

| State | Retardance of element 26 | Retardance of element 27 |
|---|---|---|
| 1 | λ/2 + 0.03λ | λ/4 |
| 2 | λ/2 | λ/4 − 0.03λ |
| 3 | λ/2 − 0.03λ | λ/4 |
| 4 | λ/2 | λ/4 + 0.03λ |

All these refer to wavelengths of light having a wavelength centered on the primary operating wavelength of 546 nm. This illustrates the case for excursions of +/−0.03λ, but it is appropriate to think of the excursion as an operating parameter δ, and larger or smaller values of δ may be preferred according to what best reveals structures in the sample at hand.

While the table above shows a system of 4 states, a system with N equally-spaced states can be developed using the following equations to calculate the retardance of the i-th state:

$$R_{26}(i)=\lambda/2+\cos(i\pi/N)\delta \qquad [1]$$

$$R_{27}(i)=\lambda/4+\sin(i\pi/N)\delta \qquad [2]$$

The relative orientation of the retarder 22 to linear polarizer 21, and that of linear polarizer 28 to retarder 27, must be chosen in concert so that the assemblies 120 and 121 form a pair which is nearly in mutual extinction rather than maximum transmission. This ensures that the states of the circular polarizer and the modulated elliptical polarizer are at opposite poles. The choice to deviate by δ=+/−0.03λ around the mean operating states of λ/2 and λ/4 defines the distance from the pole, which is given by (δ/λ)*360 degrees. For the example given, the latitude corresponds to 79.2 degrees.

Note that each LCVR retarder expresses a small, periodic excursion about its mean operating point. Since the excursion is periodic, an indefinite number of trips can be taken around the Poincare sphere in either direction. Since only a small variation in retardance is needed, a relatively thin liquid crystal layer can be used such as a 5 micron thick layer of MLC-6080 from Merck (Darmstadt, German), where the substrates which form the liquid crystal cell have been treated by buffing or other means to produce a twist-free pi-cell orientation. Such a cell responds very rapidly, with a time of 5 ms or less, so can produce up to 100 states per second or more.

Alternatively, analyzer 121 can be realized using a retarder 26 which is a ¼ wave retarder made of Nitto quarter-wave retardance film with its fast axis oriented at angle α; retarder 27 which is an LCVR having its fast axis at angle β=α+/−45 degrees, i.e. offset by 45 degrees from the fast axis of item 26. Linear polarizer 28 has either its extinction axis or its transmission axis offset γ of approximately 5 degrees from the fast axis of retarder 27. Either way, the effect of varying the retardance of LCVR element 27 over a range of λ is to traverse a latitude line at which is offset by 2γ from a pole on the Poincare sphere. This is understood by analysis using the Jones calculus; or more intuitively by considering the behavior for light propagating backwards through elements 28, 27, and 26. Light which is linearly polarized by linear polarizer 28 is transformed by the LCVR to have a polarization state which describes a circle on the Poincare sphere having a diameter 2γ, centered on the equatorial point having a longitude of 2β. Retarder 26 transforms this circle to be centered about one pole or the other on the Poincare sphere.

For this arrangement, one may express four states by choosing any four retardances a, a+λ/4, a+λ/2, and a+3λ/4. Or, a finer set of states can be obtained by choosing N states where the retardance of the i-th state is $$R_i=a+i\lambda/N \qquad [3]$$

One may traverse the states in either order, either by increasing i from 1 to N, or decreasing it from N down to N. But either way, after one trip around the Poincare sphere, LCVR 27 expresses a value of retardance which is different by λ from what it had at the beginning of the trip. Since LCVR elements have finite control range, and can typically only produce of order 1-2 waves retardance, one cannot continue to perform repeated trips around the sphere because the LCVR will hit the limit of its retardance range. At that point, one must either reverse direction, and traverse the latitude ring backwards; or reset the system more rapidly to its starting point. Either way, the action is discontinuous, which is not optimum for user comfort and acuity.

Another embodiment of the invention uses the same entrance polarizer 120 to produce circularly polarized light, but constructs the analyzer polarizer 121 using a mechanically rotating element. Retarder 26 is a low-value retarder, having a retardance of 0.03λ, and its axis changes as this component is mechanically rotated about its axis, which is approximately coincident with the optical axis. Such a retarder can be constructed from two retarders having low, but different, values of retardance. For example, a 125 micron thick piece of X-cut quartz may be combined with a 123 micron thick piece of X-cut quartz, with their fast axes crossed. The resulting assembly has a retardance of approximately 17.8 nm of retardance, making it 0.033λ for 546 nm light. The rotating element should be constructed with low wedge, preferably 30 seconds of arc or less, to avoid optomechanical deflection of the image as it is turned. The pieces of quartz may be cemented, or joined in some other way according to the know techniques of optical fabrication. Retarder 27 is a λ/4 plate which has its fast axis offset by 45 degrees from the extinction axis of linear polarizer 28.

The behavior of the assembly 121 can be understood as follows. Retarder 27 and linear polarizer 28 form a circular polarizer, which rotating low-value retarder 26 converts into an elliptical polarizer of fixed ellipticity, whose latitude is determined by the retardance of element 26; and variable longitude, determined by its instantaneous orientation as it rotates.

This arrangement produces a continuous action, akin to having an infinite number of states, and the rate at which it performs laps around the sphere can be mechanically adjusted. The analyzer polarizer performs a circuit around the Poincare sphere once for every half-revolution of retarder 26.

Another embodiment which uses mechanical rotation uses the same entrance polarizer 120 to produce circularly polarized light, but analyzer polarizer 121 comprises different elements. Retarder 26 may be omitted, and retarder 27 has a value slightly of λ/4+δ. Its fast axis is oriented at 45 degrees to the extinction axis of linear polarizer 27, and both these elements rotate together relative to the rest of the apparatus. This has the effect of analyzing in an elliptical state whose ellipticity axis is mechanically rotated.

In another embodiment, analyzer polarizer 121 comprises retarder 26 which has a retardance of λ/2+6, and is mechanically rotated. Retarder 27 is a quarter-wave plate and has its fast axis oriented at 45 degrees to the extinction axis of linear polarizer 28. The polarization state of these two elements (27 and 28) is the same as that of entrance polarizer 120. Retarder 26 transforms the state of polarization to its near opposite, so the overall arrangement is that the analyzer and entrance polarizers are nearly opposed on the Poincare sphere.

Variations of these embodiments are possible, where the rotating element is part of the entrance polarizer rather than the analyzer polarizer. This can relax the requirement for low wedge in the rotating component since it is placed in the illumination path rather than the imaging path, so wedge does not translate directly to a perceived image shift in the eyepieces. Or, embodiments are possible where both components rotate relative to the sample, using the principles of the invention just set forth.

Another aspect of the invention involves the recognition that both the entrance polarizer and the analyzer polarizer exhibit chromatic effects which can move the location of their maximally transmitted state across the surface of the Poincare sphere, to a degree that is significant compared to the magnitude of the birefringent structures involved. For example, an eyepiece viewing system would be valuable to detect spindles in oocytes in in vitro procedures and embryology experiments. The birefringence of a spindle is typically 2-3 nm, corresponding to 1.3-2.0 degrees on the sphere. Yet for a film λ/4 plate, the location on the sphere varies with wavelength by 0.2 degrees/nm, or 6 degrees over the 30 nm spectral breadth of the interference filters used in the prior art. Quartz waveplates are similar, expressing a 5 degree shift.

The invention recognizes that this shift is significant, and that chromatic effects in the analyzer polarizer may compound, or cancel, or simply render more complicated, the chromatic effects developed in the entrance polarizer; and further, that by choosing a preferred orientation of components, this large and uncontrolled term can be eliminated.

By reducing or eliminating chromatic errors, and controlling the relative orientation of components in the manner shown below, one obtains a lower and more predictable background, against which the modulation of birefringent structures is more readily seen, with less need for operator skill and with less eyestrain.

It is also possible to use broadband light rather than quasi-monochromatic light, with the benefit of a more natural view, and higher signal levels. This reduces the disparity in brightness levels when switching between microscopy modes, as described earlier. One may use a 50 nm, or 100 nm bandpass filter; or one may permit the entire visible range to be viewed, though in situations where the sample may have sensitivity to violet light it may be desirable for that reason to place a long-pass filter such as a filter or GG470 filter from Schott (Duryea Pa.) in the beam path prior to the sample.

One embodiment of the invention which markedly reduces, or eliminates, chromatic effects is the following. The elements are arranged as shown in FIG. 2. Entrance polarizer 120 is composed of linear polarizer 21 with its extinction axis at 0 degrees and quarter-wave retarder 22 with its fast axis at 45 degrees. Turning to the analyzer polarizer, retarder 26 is a quarter-wave retarder of the same material used in 22, with its fast axis at 135 degrees, crossed to that of element 22. Retarder 27 is an LCVR with its fast axis at 90 degrees, and linear polarizer 28 has its extinction axis oriented at 85 degrees.

The operation of these elements can be analyzed formally using the Jones calculus, but the achromatic behavior is easily understood intuitively as follows. When there is no sample, elements 22 and 26, being like retarders with axes crossed, cancel entirely. Thus, the apparatus has essentially no chromatic defects which interfere with the production of a uniform background for an eyepiece view. A more detailed analysis reveals that the sample birefringence and the LCVR introduce chromatic effects, but they are an order of magnitude (or more) smaller than those arising from the quarter wave plates when the entrance polarizer and analyzer polarizer are not constructed properly and placed in a controlled orientation to one another.

Similarly, the mechanically rotating system can be build in an achromatic fashion. The entrance polarizer 120 is the same as in the previous example. The analyzer polarizer 121 comprises waveplate 26 made of opposed quartz pieces to yield a net retardance of 17.8 nm, which rotates; and waveplate 27 made of the same material as waveplate 22, oriented with its fast axis at 135 degrees, and linear polarizer 28 with its extinction axis at 90 degrees. Again, chromatic effects from element 22 and 27 cancel entirely, and one is left with only the residual effects of the lower-valued retarder 26. A marked increase in uniformity and color constancy is obtained compared to the prior art which did not control the construction and relative orientation of components 120 and 121 to achieve an achromatic operation.

The arrangement where element 26 is a λ/2 wave LCVR, and element 27 is a λ/4 wave LCVR, as described above and used in the prior-art LcPolScope and Oosight systems, has a large amount of chromatic error, with contributions from each retarder element.

Figure 5:
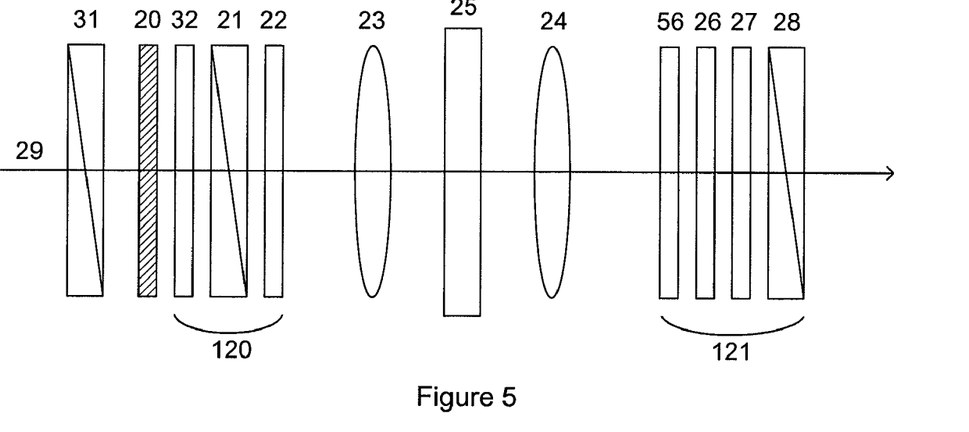
FIG. 5 is a schematic drawing implementing the invention in a fourth optical arrangement, where the entrance polarizer comprises retarder 32, linear polarizer 21, and retarder 22. Analyzer polarizer comprises retarder 56, retarder 26, retarder 27, and linear polarizer 28.
Figure 6:
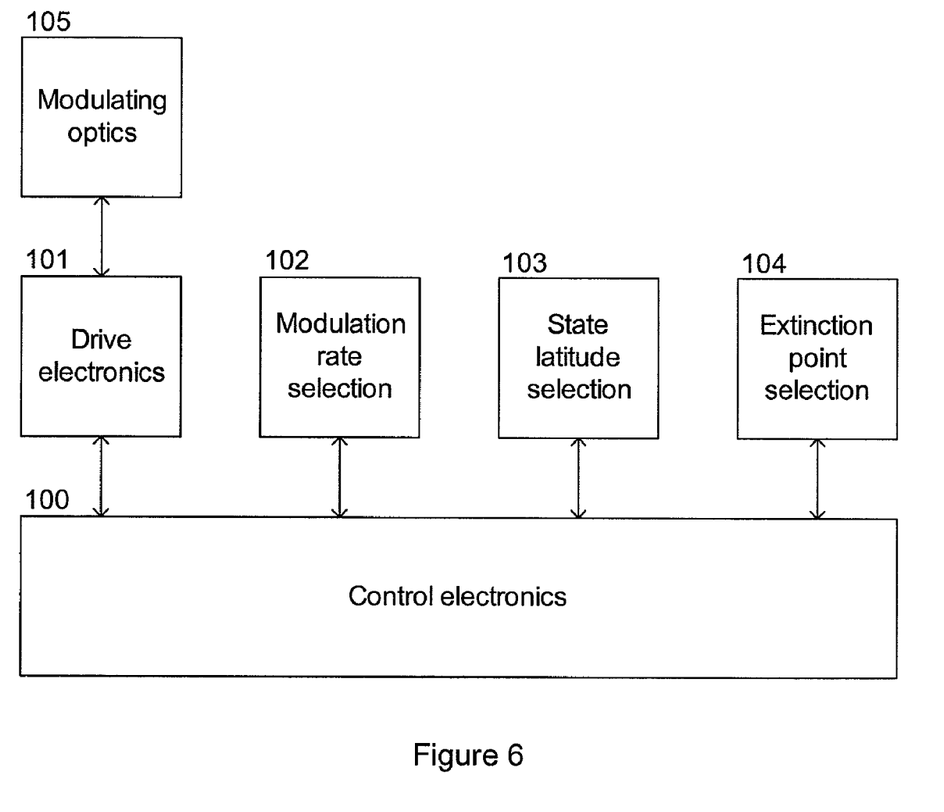
FIG. 6 is a block diagram showing the control electronics 100 which receives control signals from optional user modulation rate selection element 102, state latitude selection element 103 and extinction point selection element 104, and produce signals in communication with drive electronics 101 which causes the modulation optics 105 to produce one or more polarization states at the entrance polarizer or analyzer polarizer.

An achromatized embodiment according to the present invention is shown in FIG. 5. Again, entrance polarizer is comprised of linear polarizer 21 with its extinction axis at 0 degrees, and retarder 22 is a λ/4 plate with its fast axis at 45 degrees, made from Nitto quarter-wave film. Retarder 56 is a λ/4 plate of the same material as element 22, with its fast axis at 0 degrees. Retarder 26 is an LCVR whose fast axis is at 90 degrees. Retarder 27 is an LCVR whose fast axis is at 135 degrees, and linear polarizer 28 has its extinction axis at 90 degrees. Both linear polarizers are Sanritz LLC2-5618 type. The values used in the LCVR elements are:

$$R_{26}(i) = 136.5\text{nm} + \cos(\pi i/N)*\delta \quad [4]$$

$$R_{27}(i) = 136.5\text{nm} + \sin(\pi i/N)*\delta \quad [5]$$

where $\delta = 17$ nm in an exemplary embodiment, and retardance is specified as measured at 546 nm. The LCVR elements use 8 micron layers of LC material ZLI-1132, as the birefringence dispersion of this material matches that of the Nitto film.

In this arrangement, elements 56 and 26 cancel perfectly when $\cos(\pi i/N) = 0$, since they have identical retardance and their fast axes are crossed. Similarly, element 27 cancels element 22 perfectly when $\sin(\pi i/N) = 0$, as their values match and their fast axes are crossed. The only chromatic behavior is of order $\delta$, which is directly related to the modulation which is sought.

This embodiment yields markedly better uniformity of intensity and hue than the prior art arrangements. In one preferred embodiment, filter 20 is a 450 nm long-pass filter and the microscopist obtains a white-light view of the sample.

Like the earlier embodiment using two LCVR elements, this provides for rapid, continuous motion since only small, periodic adjustment is required from each LCVR as the states of the system traverse the Poincare sphere.

Another preferred embodiment is like the previous one, except element 56 is another LCVR whose fast axis is at 0 degrees. It may be driven to a constant retardance of 136.5 nm, or it may function in a push-pull arrangement with element 26, with retardances of:

$$R_{56}(i) = K + \cos(\pi i/N)*\delta/2 \quad [6]$$

$$R_{26}(i) = K - \cos(\pi i/N)*\delta/2 \quad [7]$$

This has the convenience that K can be any convenient value. Also, since K is unimportant and only the difference $R_{56} - R_{26}$ affects the measurement, common-mode drift in K—as may occur if all LCVR elements experience thermal drift—cancels out. So it is relatively rugged in this regard.

Other arrangements can be achromatized, using the examples above as guides, and using techniques such as Jones calculus to model the proposed design.

Another aspect of the present invention is the recognition that the calibration step in the prior art can be simplified from its complex form, to a simple step that can be performed visually by a user at the eyepieces.

Specifically, the prior-art calibration of the LcPolScope, SpindleView, Oosight, and Abrio had two aims. First, it sought to find the setting of the LCVR elements which minimized the signal; this is the so-called extinction state. The search for the extinction state is complicated in the prior art by the fact that different colors may be best extinguished at different LCVR settings, so one does not see a uniform darkening of the scene as the extinction state is approached; instead, one sees changing hues mixed with changing brightness. The best minimum is determined by the output of a quantitative, photometric camera, which weights the various color components in a relatively equal way. But a visual assessment is not always reliable when using the embodiments of the prior art.

The next calibration step was to set one LCVR element to a distance $\delta$ from the value it had at the extinction state and the signal strength was measured; let us term this the $\delta$ state. Finally, signals were measured at a variety of settings for each LCVR, in an attempt to match the $\delta$ state signal. This is equivalent to locating states which lie on a latitude line on the Poincare sphere.

The human eye, being neither linear nor time-invariant in its response, is ill-equipped to make such an assessment. Thus, it is not practical to set states such as 11*a*-11*h* based on a visual assessment.

In some embodiments, the invention provides direct visual setting of LCVR calibration. First, by providing optical embodiments which are more predictable, spatially uniform, and achromatic than the prior art, the eyepiece view shows all colors being extinguished more or less together. In a preferred embodiment, the control electronics provide a calibration mode where the control electronics establish the states corresponding to $\delta = 0$, and the user seeks the best extinction state, based on a visual assessment. Using controls such as a touchpad, knobs, or GUI elements, the user input is used to adjust the drive to the LCVR elements until the user believes that best extinction is obtained. This can be done by altering the mean voltage supplied to the LCVR, with independent inputs for each LCVR.

Second, the present invention provides for rapid cycling around a latitude on the Poincare sphere. Since the states span the latitude circle 12 more or less evenly, and these states correspond to equal visual intensity when the apparatus is properly calibrated, another embodiment of the invention is to establish or revise the calibration while the apparatus cycles continuously through states with a nonzero $\delta$ such as $\delta = 0.03\lambda$. Using controls such as a touchpad, knobs, or GUI elements, the user input is used to adjust the drive to the LCVR elements, while the user observes the variation of the eyepiece view. More specifically, what is adjusted is the mean value of retardance about which the excursion of $\delta$ (or $\delta/2$ for push-pull elements) is made. When the signal is most steady during the course of the sequence of states, the best state has been obtained.

Figure 3:
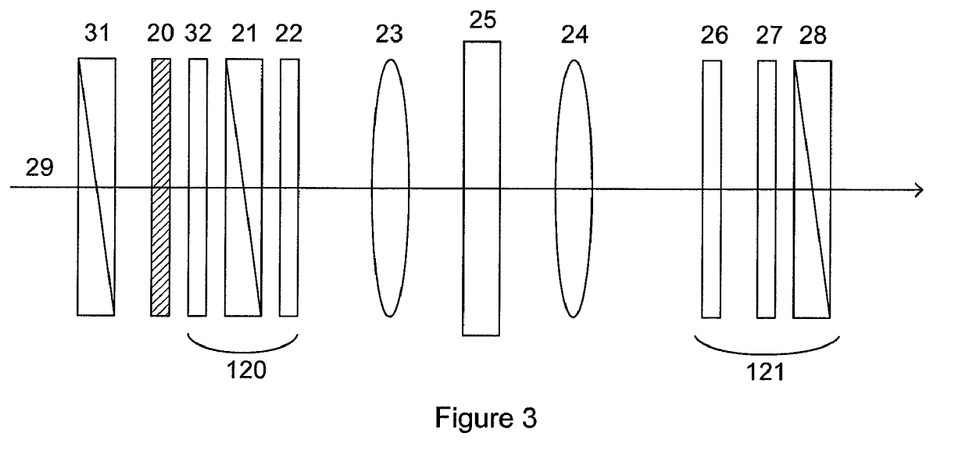
FIG. 3 is a schematic drawing implementing the invention in a second optical arrangement, where the entrance polarizer 120 further comprises retarder 32 on the entrance face.

Another aspect of the invention is illustrated in FIG. 3. In this embodiment, which is otherwise like the embodiments of FIG. 2, entrance polarizer 120 includes a waveplate element 32 on the entrance face of linear polarizer 21. This element is a $\lambda/4$ retarder with its fast axis oriented at 45 degrees relative to the extinction axis of polarizer 21. The effect is that entrance polarizer 120 both accepts, and produces, circularly polarized light. It is accordingly termed a symmetric circular polarizer.

When element 120 is placed in a linearly polarized beam, it suffers an insertion loss of 50%. Linear polarizer 31 indicates a polarizer preceding element 120 along the optical axis, which produces a linearly polarized beam. The loss is not unduly high—it is the same as occurs when element 120 is placed in an unpolarized beam—and it is independent of how the polarization axis of 31 is oriented. So the apparatus of FIG. 3 can be placed after a variably oriented linear polarizer 31, such as may be present in a Hoffman microscope configuration, without its performance changing as the linear polarizer axis is rotated.

This independence makes it convenient to operate a microscope in Hoffman mode without needing to remove the birefringence eyepiece viewing apparatus from the beam.

Figure 4:
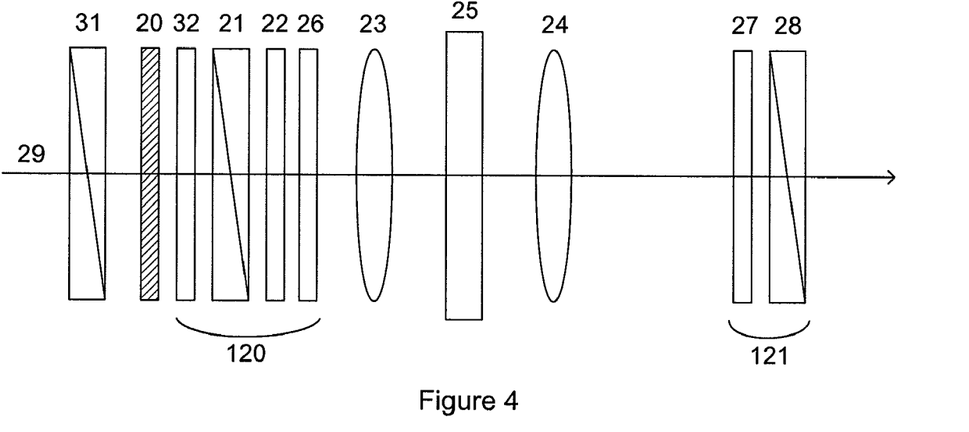
FIG. 4 is a schematic drawing implementing the invention in a third optical arrangement, where the entrance polarizer comprises retarder 32, linear polarizer 21, retarder 22, and retarder 26. Analyzer polarizer 121 comprises retarder 27 and linear polarizer 28.

FIG. 4 illustrates that in practicing the invention, one may interchange whether the entrance polarizer is a fixed circular polarizer while analyzer polarizer is dynamic; and instead may have an apparatus where the entrance polarizer is dynamic and the analyzer polarizer is fixed. The decision of which approach to take may be taken based on design factors such as cost of materials, aperture and acceptance angle of the components involved, modularity of the system, and so on, as will vary with the case at hand.

While the invention has been illustrated with examples drawn from microscopy, it is possible to make apparatus for viewing macroscopic samples as well, using the same principles. In some embodiments, condenser lens 23 is omitted, or imaging lens 24 is omitted, or both are omitted. When present, these elements need not be simple lenses, but may contain multiple elements in order to achieve various optical goals, as is known in the art of lens design and optical system design.

Similarly, elements which are depicted as separate elements may be joined together when that does not conflict with mechanical rotation; or may have windows, optical coatings, or other elements joined to them according to the needs at hand and the known art of optical fabrication. Such variations and others will be evident to those familiar with polarization optics and opto-mechanical design, and the examples above are intended to illustrate the invention rather than to limit its scope, which should be limited only by the attached claims.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A system for visualizing birefringent structures in samples, comprising:
    a source of light,
    an entrance polarizer which receives incident light in an incident state of polarization and transmits a portion thereof,
    wherein light exiting the entrance polarizer has a first selected state of polarization;
    an analyzer polarizer which receives light incident upon it and selectively transmits a portion corresponding to a second selected state of polarization; and
    control electronics,
    wherein one of said first and second states of polarization is substantially circular, and wherein the other of said first and second selected polarization states is a target state, produced in response to a control signal from the control electronics;
    wherein four or more target states of polarization are produced per second.

2. The system of 1 wherein the entrance polarizer state is substantially circular and the analyzer polarizer state is the target state that changes in response to the control signal.

3. The system of 1 wherein the analyzer polarizer state is substantially circular and the entrance polarizer state is the target state that changes in response to the control signal.

4. The system of 1 wherein the target states lie substantially at same latitude on Poincare sphere, and said latitude is within 20 degrees of one of the poles.

5. The system of claim 4 in which the target states are traversed eastward on the Poincare sphere.

6. The system of claim 4 in which the target stats are traversed westward on the Poincare sphere.

7. The system of 1 in which there are 8 or more target states.

8. The system of 1 in which there are 16 or more target states.

9. The system of claim 1, wherein the control electronics comprise a user input allowing manipulation by a user of at least one characteristic of at least one of the polarizer states.

10. A system for visualizing birefringent structures in samples, comprising:
    a source of light,
    an entrance polarizer which receives incident light in an incident state of polarization and transmits a portion thereof,
    wherein light exiting the entrance polarizer has a first selected state of polarization;
    an analyzer polarizer which receives light incident upon it and selectively transmits a portion corresponding to a second selected state of polarization; and
    control electronics,
    wherein one of said first and second states of polarization is substantially circular, and wherein the other of said first and second selected polarization states is a target state of polarization produced in response to a control signal from the control electronics;
    wherein a control responsive to user inputs provides direct adjustment of the location of the target states on the Poincare sphere.

11. The system of 10 in which the target states line on a circle on the Poincare sphere and the user adjusts the location of the center of the circle.

12. The system of 10 in which the target states lie on a circle on the Poincare sphere and the user adjusts the diameter of the circle.

13. The system of 11 in which four or more target states are produced per second during the time that the user adjusts the location of the center of the circle.

14. A system for visualizing birefringent structures in samples, comprising:
    a source of light,
    an entrance polarizer which receives incident light in an incident state of polarization and transmits a portion thereof, said entrance polarizer comprising in optical series a linear polarizer and a waveplate having a first retardance value and first fast axis orientation,
    an analyzer polarizer which receives light incident upon it and selectively transmits a portion corresponding to a second selected state of polarization, said analyzer polarizer comprising in optical series a waveplate having a second retardance value and second fast axis orientation, and a linear polarizer,
    control electronics,
    wherein one of said first and second states of polarization is substantially circular, and wherein the other of said first and second selected polarization states is a target state of polarization produced in response to a control signal from the control electronics;
    wherein said first fast axis orientation and said second fast axis orientation are oriented at substantially right angles, and said first retardance value and second retardance value are matched to within $0.06\lambda$ or less.

* * * * *